US008998891B2

(12) United States Patent  (10) Patent No.: US 8,998,891 B2
Garito et al.  (45) Date of Patent: Apr. 7, 2015

(54) TRI-FREQUENCY ELECTROSURGICAL INSTRUMENT

(75) Inventors: Jon C. Garito, Oceanside, NY (US); Alan G. Ellman, Oceanside, NY (US)

(73) Assignee: Ellman International, Inc., Hicksville, NY (US)

( * ) Notice: Subject to any disclaimer, the term of this patent is extended or adjusted under 35 U.S.C. 154(b) by 2020 days.

(21) Appl. No.: 11/897,035

(22) Filed: Aug. 30, 2007

(65) Prior Publication Data

US 2009/0062786 A1    Mar. 5, 2009

(51) Int. Cl.
*A61B 18/12* (2006.01)
*A61B 18/14* (2006.01)
*A61B 18/00* (2006.01)

(52) U.S. Cl.
CPC .............. *A61B 18/12* (2013.01); *A61B 18/1206* (2013.01); *A61B 18/14* (2013.01); *A61B 2018/00178* (2013.01); *A61B 2018/0066* (2013.01); *A61B 2018/00732* (2013.01); *A61B 2018/1273* (2013.01); *A61B 2018/128* (2013.01)

(58) Field of Classification Search
CPC ........... A61B 18/1206; A61B 18/1233; A61B 2018/00577; A61B 2018/00589; A61B 2018/00595; A61B 2018/00601; A61B 2018/00607; A61B 2018/0063; A61B 2018/1206; A61B 2018/1253; A61B 2018/126; A61B 2018/128; A61B 2018/1273
USPC .................................................... 606/32–50
See application file for complete search history.

(56) References Cited

U.S. PATENT DOCUMENTS

| 3,058,470 | A | * | 10/1962 | Sanden et al. | 606/37 |
| 4,185,927 | A | | 1/1980 | Uttech | |
| 4,188,927 | A | * | 2/1980 | Harris | 606/38 |
| 4,378,801 | A | * | 4/1983 | Oosten | 606/37 |
| 5,954,686 | A | * | 9/1999 | Garito et al. | 604/37 |
| 6,652,514 | B2 | * | 11/2003 | Ellman et al. | 606/37 |
| 7,094,231 | B1 | * | 8/2006 | Ellman et al. | 606/37 |
| 7,674,261 | B2 | | 3/2010 | Garito et al. | |
| 2004/0054365 | A1 | * | 3/2004 | Goble | 606/34 |

FOREIGN PATENT DOCUMENTS

EP    1707147    10/2006

OTHER PUBLICATIONS

European Search Report dated Jan. 23, 2009 for European Patent application No. 08252879.5; 9 pages.

* cited by examiner

*Primary Examiner* — Ronald Hupczey, Jr.
(74) *Attorney, Agent, or Firm* — Ganz Pollard, LLC

(57) ABSTRACT

An electrosurgical instrument that is capable of generating high-quality RF energy carriers at one of three different frequencies and combining any of the three carriers with any one of four electrosurgical mode waveform modulations and selectively supplying the modulated carriers to either a monopolar or a bipolar handpiece. In a preferred embodiment, the first carrier frequency is in the range of about 3.8-4.0 MHz, the second carrier frequency is in the range of about 1.7-2.0 MHz, and the third carrier frequency is in the range of about 400-600 KHz.

26 Claims, 4 Drawing Sheets

TRI-FREQUENCY ELECTROSURGICAL INSTRUMENT

The invention is directed to an electrosurgical instrument or apparatus, and in particular to an electrosurgical instrument that operates with three different carrier frequencies.

BACKGROUND OF INVENTION

Electrosurgical instruments are well known and widely used in the medical, dental, and veterinarian fields. They offer the capability of precision cutting with electrosurgical currents using a handpiece with needle, ball, or loop electrodes in a monopolar operating mode, or convenient coagulation using a forceps in a bipolar operating mode. Ellman International, Inc., of Oceanside, N.Y. makes available an electrosurgical instrument which provides on its front panel connectors for receiving the plug of a unipolar handpiece and a ground or indifferent plate, as well as a connector for receiving the plug of a bipolar forceps cable.

In a typical surgical setting, a surgeon may first use the unipolar handpiece to perform a desired cutting procedure and then desire to use the bipolar forceps for coagulation of blood vessels because of its unique ability to coagulate in a fluid field. One possible solution which maintains the requisite sterile field while still allowing the surgeon to unplug and plug in different devices from or to the instrument is described in U.S. Pat. No. 5,954,686, whose full contents are herein incorporated by reference. In the solution proposed in this patent, the electrosurgical instrument is configured to generate two MHz carrier frequencies, the higher one of about 4 MHz for operation in the CUT, and CUT/COAG modes, and the lower one of about 2 MHz for operation in the HEMO and FULGURATE modes. These four operating modes typically are represented by CUT: full-wave rectified and filtered CW output with maximum average power; CUT/COAG: full-wave rectified but unfiltered, deeply modulated (at 37.5 or 75 Hz rate) envelope output with approximately 70% average to peak power ratio; HEMO: half-wave rectified and unfiltered, deeply modulated (at 37.5 or 75 Hz rate) envelope output with approximately 35% average to peak power ratio; FULGURATE (or Spark-Gap Wave): deeply modulated (3.6 KPPS random rate) with approximately 20% average to peak power ratio. Selection of the bipolar mode will normally select the HEMO mode.

SUMMARY OF INVENTION

The principal object of the invention is an electrosurgical instrument capable of providing optimal electrosurgical energy for cutting, coagulation, and fulguration using either the monopolar or bipolar mode of the instrument.

We have found that the instrument described in U.S. Pat. No. 5,954,686, while very well suited for many surgical procedures, may not be fully satisfactory for specialties in what can be described as liquid medium surgical procedures. Such procedures include, for example, gross surgical procedures such as abdominoplasties, body sculpturing, thigh and buttock lift surgery, brachioplasty or internal surgery on organs, or surgical procedures where large volumes of tumescent liquid anesthic, saline, or water, either dextrose or glycerine, are irrigated into the surgical site such as in arthroscopic procedures, or urologic procedures such as transurethal resections, resection of bladder tumors, polyp removal, and kidney resection to remove stones. It appears that the use of MHz frequencies for such procedures may not always be optimum for both cutting and coagulation. However, certain applications still require an instrument which provides high output radio-frequency (RF) energy for delicate, precise and quick-healing cutting procedures, but with low leakage currents. To the best of our knowledge, there is no commercially-available instrument that provides high output radio-frequency (RF) energy for delicate, precise and quick-healing cutting procedures with low leakage currents using a unipolar handpiece that also provides high-quality RF energy best suited for coagulation for use with a bipolar handpiece, and that also provides high output electrosurgical currents at lower frequencies for those surgeons that prefer lower frequency electrosurgical currents for liquid medium surgical procedures.

These objects are achieved in accordance with one aspect of the invention by an electrosurgical instrument that is capable of generating high-quality RF energy at a first MHz carrier frequency best suited for delicate, precise, and quick-healing cutting procedures with low leakage currents using a monopolar handpiece, and also provides high-quality RF energy at a second MHz carrier frequency coagulation for use with a bipolar handpiece, and also provides high-quality electrosurgical energy at a third KHz carrier frequency best suited for performing liquid medium surgical procedures with either the monopolar or bipolar handpiece.

In another aspect of the invention, a feature of the electrosurgical instrument of the invention is the capability to generate three carrier frequencies, four operating modes represented by different electrical modulation waveforms, and to combine under control of the user each of the three carrier frequencies with any of the electrical modulation waveforms representing the different operating modes to form a unique set of electrosurgical currents, and to deliver such electrosurgical currents to either of the connected monopolar or bipolar handpieces. Preferably, two of the three carrier frequencies are in the MHz range, and the third carrier frequency is in the KHz range.

By "electrosurgical mode" as used herein is meant a configuration of the instrument represented by a distinct setting within a computer program or any physical machine interface, in which the same user input will produce perceived different results than it would in other settings. Typically, the electrosurgical mode is established by the user actuating instrument settings on the front panel or by the user actuating buttons on a handpiece or a footswitch connected to the instrument. Mode examples include monopolar and/or bipolar activation, and a user selection of carrier frequency and modulating waveforms representing one of the four operating modes. Typically, the instrument configuration remains at the last user selection until changed by the user. Generally, the modulation frequencies will vary from 0 Hz to 5 KHz. Specifically, in accordance with the invention, the four operating electrosurgical modes are represented by CUT: CW output with maximum (or 100%) average power obtained with full-wave rectified and filtered carrier waveforms; CUT/COAG: approximately 70% average power output achieved with full-wave rectified but unfiltered, deeply modulated (at approximately 100 Hz rate) output waveforms; HEMO: approximately 50% average power output achieved with half-wave rectified and unfiltered, deeply modulated (at approximately 60 Hz rate) output waveforms; FULGURATE (or Spark-Gap Wave): approximately 20% average power output achieved with deeply modulated (3.6 KPPS random rate) output waveforms. The percentages given are with respect to the maximum value.

The various combinations of carrier frequency and modulation combined with the choice of handpiece selected by the user/surgeon produces a remarkable number of active electrosurgical currents with a wide variety of tissue effects. Three different carriers each with four different modulations applicable to tissue via either of two different handpieces provides a total of 12 different electrosurgical currents via the two handpieces and provides, in essence, at selected power levels varied levels of coagulation and cutting. This includes not only the usual high power tissue cutting currents as well as low power bleeder coagulation currents but also more modest tissue effects with controllable lateral heat spread better suited around critical anatomical parts for hemostasis as well as lower frequency currents for application to liquid-heavy surgical procedures. While, generally speaking, the monopolar handpiece is preferred for smooth cutting and combined cutting and coagulation, whereas the bipolar handpiece with its two active ends concentrates the electrosurgical currents between the ends, and is thus preferred for local hemostasis with lower power, many surgical situations may arise where it is preferred that higher power electrosurgical currents are applied with the bipolar handpiece and lower power electrosurgical currents with the monopolar handpiece.

In a preferred embodiment, the first carrier frequency is in the range of about 3.8-4.0 MHz, the second carrier frequency is in the range of about 1.7-2.0 MHz, and the third carrier frequency is in the range of about 400-600 KHz. The preferred values are 4 MHz, 1.71 MHz and 500 KHz.

Preferably, the first, second and third carrier frequencies are derived by division by 2 upon selection from RF carrier generators at double the desired frequencies which simplifies the RF generator selection circuitry.

In accordance with a further aspect of the invention, the instrument is configured so that both a monopolar handpiece and a bipolar handpiece can be used during a surgical procedure, though not at the same time, without having to activate any switches on the instrument.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

Figure 1:
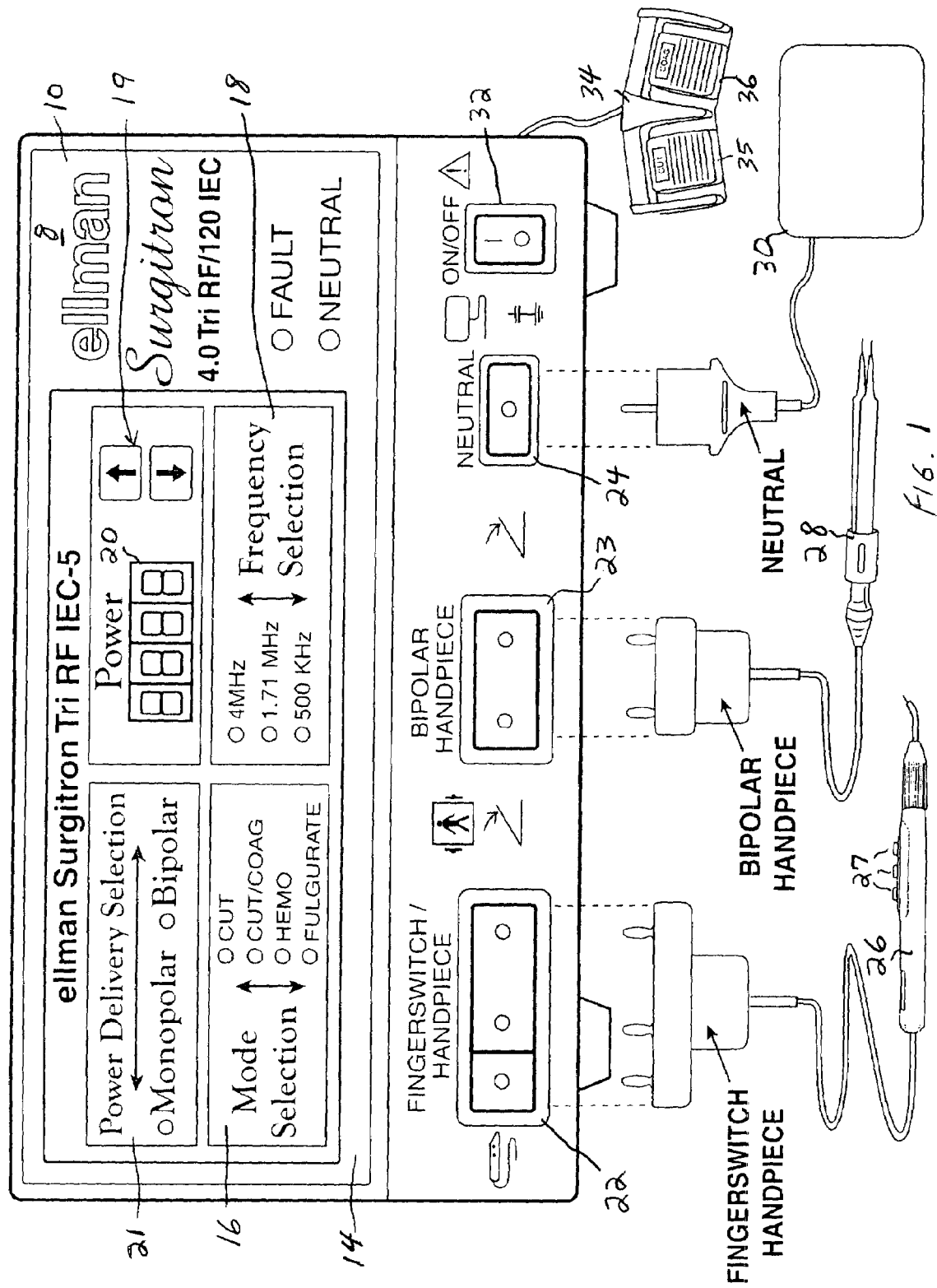
FIG. 1 is a schematic view of one form of electrosurgical instrument in accordance with the invention.

One form of the electrosurgical instrument 10 according to the invention is illustrated in FIG. 1. It comprises a console unit 8 having a box-like housing comprising at the front a control panel 14 for the instrument. The control panel includes as part of a touch panel touch switches 16 for selecting one of four electrosurgical modes comprising CUT (cutting), CUT/COAG (blended cutting and coagulation), HEMO (coagulation), and FULGURATE (spark gap tissue destruction), touch switches 18 for selecting one of three operating frequencies as illustrated, up and down touch switches 19 for controlling the power output, displayed at 20, and touch switches 21 for directing the selected operating mode to either the monopolar or bipolar handpiece. At the bottom are output female connectors 22, 23, 24 for plugging in, respectively, at the left, a fingerswitch-controlled monopolar handpiece 26; at the center a bipolar handpiece or forceps 28; and at the right a single or split neutral plate 30. An on-off power switch 32 is at the far right. The circuitry used to provide a fingerswitch-controlled monopolar handpiece may be of the type described in connection with the control unit 50 of U.S. Pat. No. 4,463,759, whose contents are herein incorporated by reference, which circuitry is in this case incorporated in the console unit 8. A connector (not shown) is provided at the side for receiving a conventional footswitch 34 having left 35 and right 36 sections. Both the monopolar and bipolar handpieces can be simultaneously connected to the console unit 8 and operated in any order without touching the console unit or the control panel when the control panel has been preset or activated at the desired powers for each of the handpieces. For example, if the surgeon determines that s/he is going to perform a cutting procedure with a particular electrode, then s/he can preset the cutting mode power on the digital display 20 to, say, 80 watts by the up/down buttons 19. (Typically, these units are designed to supply up to 150 watts of RF power to either handpiece.) For coagulation with the bipolar handpiece, s/he may desire to use, say, 50 watts, which can also be preset on the digital display 20 by the up/down buttons 19. The internal circuitry is controlled so that, when the fingerswitch monopolar handpiece is used, then RF power can be supplied to the electrode in the monopolar handpiece when a fingerswitch 27 on the handpiece 26 is depressed. However, when it is desired to use the bipolar handpiece 28, then the footswitch 34 is depressed, which then supplies RF power to the forceps of the bipolar handpiece. This result is a consequence of software control such that, while the machine mode is selected such that the fingerswitches on the monopolar handpiece can be used to apply power to the electrode (footswitch mode non-selected), only the footswitch can be used to apply power to the bipolar handpiece. This prevents power selected for the monopolar handpiece to be applied to the bipolar handpiece, and vice-versa. On the other hand, when it is not intended to use the bipolar handpiece and the footswitch mode is selected, then the footswitch can be used to operate the monopolar handpiece.

Figure 2:
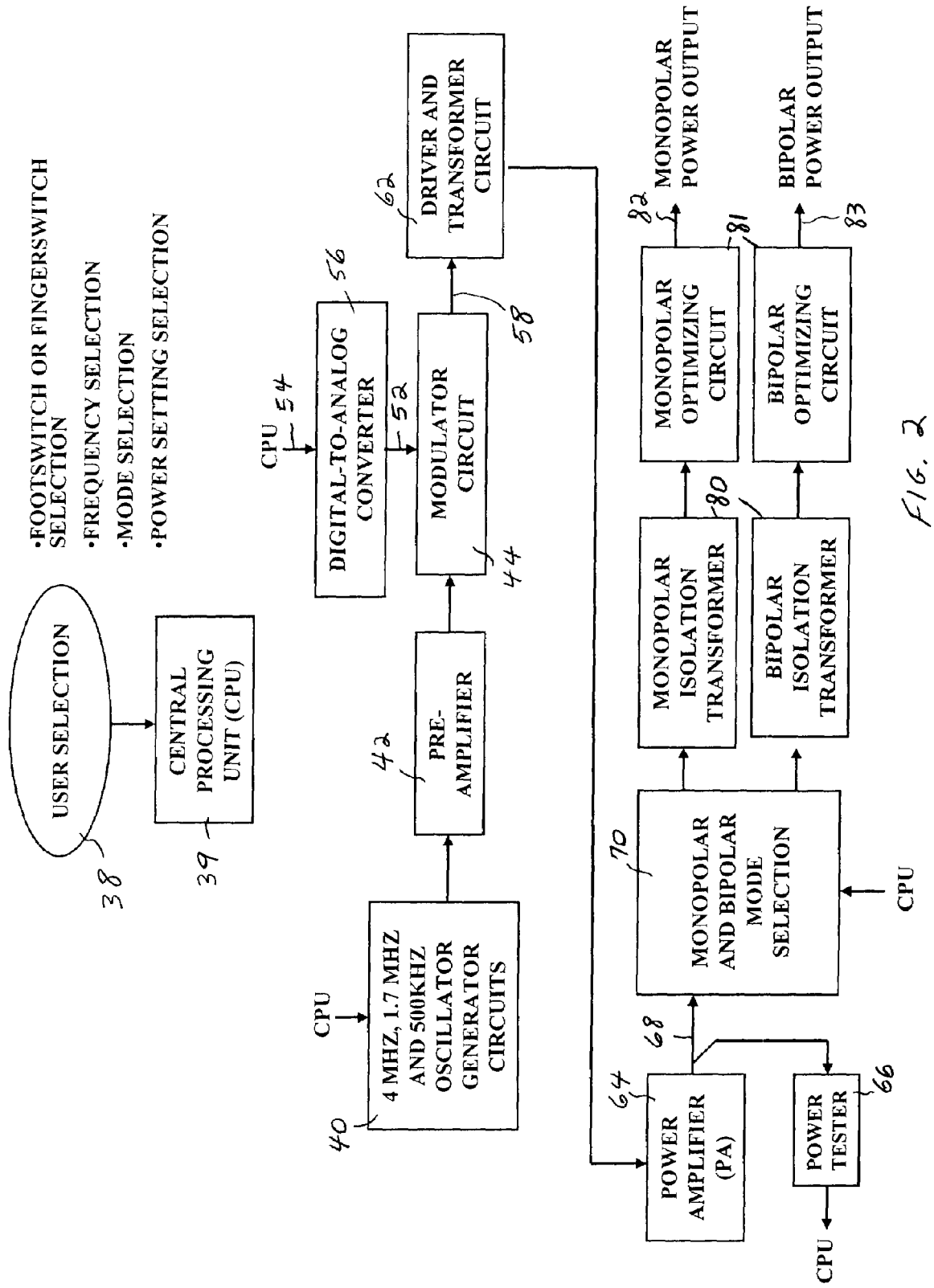
FIG. 2 is a circuit block diagram of one form of system circuitry for the electrosurgical instrument of FIG. 1.

One form of the electrical circuitry to achieve the foregoing operation is illustrated in the block diagram of FIG. 2, and is characterized by total user control. This is illustrated by the block 38 at the top indicating that the user selections of activator, i.e., fingerswitch 27 on the monopolar handpiece 26 or footswitch section 35, 36 of the footswitch 34, carrier frequency, electrosurgical mode, and power setting, are transmitted to the central processing unit (CPU) 39. The block 40 below in the upper left represents three independent conventional oscillators generating, preferably, electrosurgical carrier frequencies of 4 MHz, 1.71 MHz, and 500 KHz, previously referred to as the first, second, and third carrier frequencies (preferably derived by electrically division by 2 from RF oscillations at 8.0 MHz, 3.42 MHz, and 1 MHz, respectively). As will be explained in greater detail below, the arrow from the label CPU represents a user-generated selection signal generated by a conventional microcontroller (the CPU) under software control and inputted into the block 40 to select for current operation of one of the three operating frequencies. The microprocessor as is well known can take an input from a user and then send appropriate output signals to the other circuit blocks to implement the user's desires. All oscillators are constantly on when the power switch is activated, and the user/CPU selection 38 determines which of the first, second or third frequencies are outputted as a carrier, pre-amplified in block 42 and inputted to a conventional modulator stage 44. Also input to the modulator stage is a modulating signal 52 derived from a CPU selection signal 54 and a D/A converter 56. The D/A converter generates the modulating waveform. The modulations referred to are the pre-defined electrosurgical modes produced by the different output waveforms used for the CUT, CUT/COAG, HEMO, and FULGURATE modes as herein defined.

The RF power generating circuitry may be of the well known tube-type described in U.S. Pat. No. 3,730,188, whose contents are herein incorporated by reference, which is capable of generating a fully-rectified, filtered RF current for cutting, a full-wave rectified current for combining cutting and coagulation, and a half-wave rectified current for coagulation. Alternatively, the RF power generating circuitry can be of the well-known solid-state type capable of generating the same kinds of waveforms including fulguration. The RF circuitry, as such, is not part of the present invention, as such circuits are well-known in the prior art. What is a feature of the invention is that the RF circuitry provides three different carrier frequencies of operation, a first high frequency in the range of 3.8-4.0 MHz, a second lower frequency in the range of 1.7-2.0 MHz, and a third still lower frequency in the range of 400-600 KHz.

After the modulated carrier has been generated at 58, it is processed through a standard driver and transformer circuit 62, and a power amplifier 64 whose output is monitored for safety's sake by a power tester circuit 66 under control of the CPU. The driver and transformer circuit 62 functions to isolate the power output from the main circuit. The CPU input to the block-70 labeled Monopolar and Bipolar Mode Selection prevents both monopolar and bipolar branches from being activated at the same time. The power amplifier output 68 is inputted to a mode selection block 70 under control of the CPU. The mode selection 16 is made by the user by activating the panel setting, and by pressing switch 21 selects the monopolar or bipolar handpiece to which the electrosurgical currents will be supplied. That selection, made in conjunction with the selection 35, 36, or 27 directs the output RF energy along the upper branch or the lower branch of FIG. 2, both of which branches contain an isolation transformer 80 and a conventional optimizing circuit 81 also for operating indicators. In other words, as will be shown in the CPU flow chart, when the monopolar handpiece 26 is selected, the RF energy outputted at 82, is directed to the monopolar handpiece and the bipolar branch is disabled, and when the bipolar handpiece 28 is selected, the RF energy outputted at 83 is directed to the bipolar handpiece and the monopolar branch is disabled. The outputs 82, 83 shown at the right are directed to the connectors 22 and 23, respectively. Power delivery on the monopolar or bipolar side can be controlled by activation of the footswitch or the fingerswitch, and displayed on the front panel for user reference. Activation of more than one switch among 35, 36, or 27, will result in a fault LED glowing, and as explained prevents both the monopolar and bipolar branches from being activated at the same time.

Figure 3:
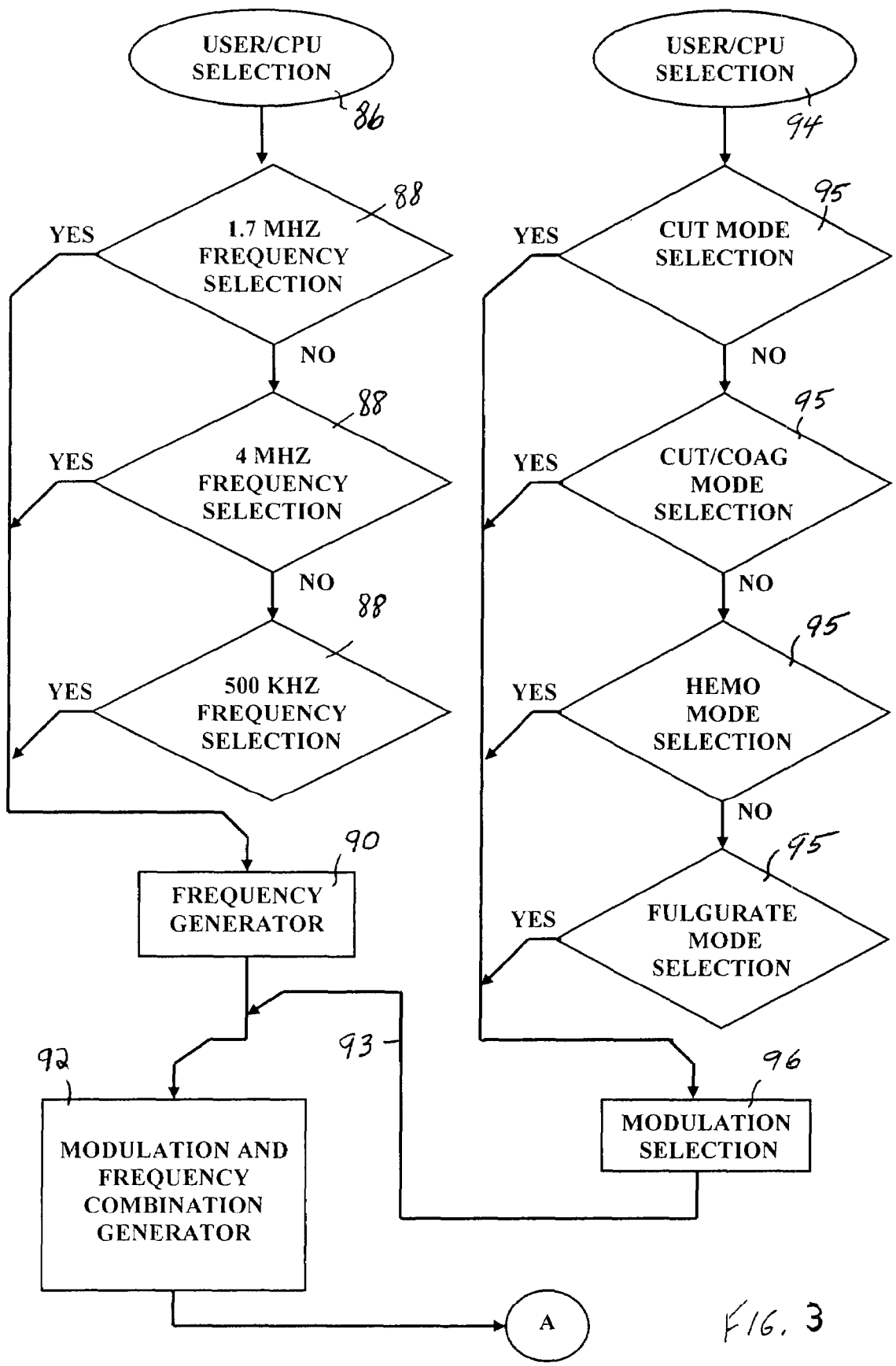
FIGS. 3 and 4 are a flow chart illustrating how the system circuitry of FIG. 2 can be software controlled and operated in accordance with the invention.
Figure 4:
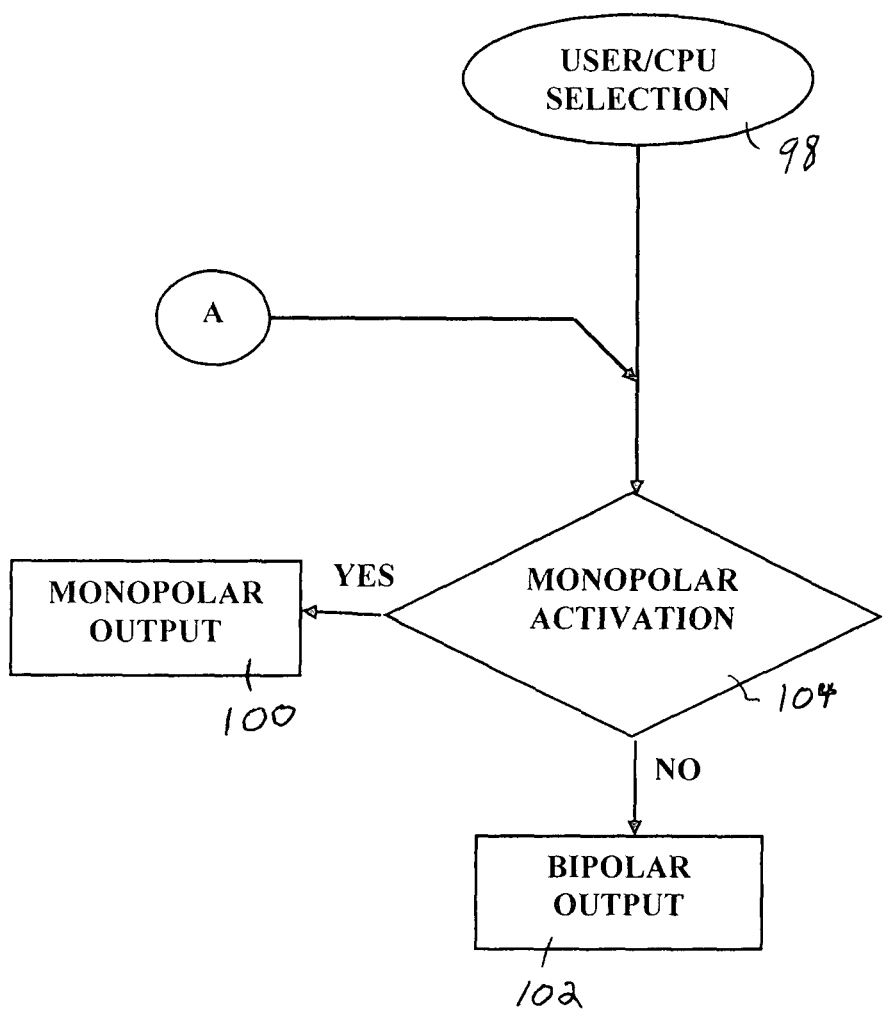

In the preferred embodiment, the instrument is software controlled with the user supplying the switch inputs. One form of software control is illustrated by the flow chart depicted in FIGS. 3 and 4. After the on-off switch 32 is toggled on, the first action by the user can be to select the carrier frequency shown at block 86 by way of a front panel button 18. The three quadrangular blocks 88 test in turn whether the user has selected the second frequency, the first frequency, or the third frequency as indicated which in turn via the microcontroller 39 (CPU) selects the associated frequency generator 90 and directs the selected carrier output to the modulator 92. The other input 93 to the modulator 92 is obtained by the user selection 94 by way of a front panel button 16 from among the four electrosurgical modes tested sequentially at 95 and the output then inputted to the modulation selection block 96. The selected modulated carrier output at A is then subject to the user selection 98 (FIG. 4) by way of a front panel button 21 of which of the two handpiece connectors 22, 23 will be activated by the delivery of the selected carrier with the selected electrosurgical mode. This mode of action differs from that described in the referenced U.S. Pat. No. 5,954,686 in that there is no automatic connection of a particular carrier frequency to a particular handpiece. In the prior patent, actuating the fingerswitches of the monopolar handpiece automatically connected the higher frequency carrier to the CUT button, and the lower frequency carrier to the HEMO button. Similar actions occurred depending on whether the footswitch was depressed.

In contrast, in the present invention, the user has the option by way of the front panel switches of connecting any one of the 12 modulated carriers previously selected to either the monopolar output 100 or the bipolar output 102 via the test block 104.

In this preferred mode of action, as illustrated in the software charts, the surgeon must touch buttons on the front panel 14 in order to activate one of the handpieces. Since button actuations are preserved in the CPU memory or an independent non-volatile memory, then it is readily easy to retain a mode of action, if desired, in which the last set of panel switches activated are retained in memory when the instrument is switched off and restored when the instrument is next turned on. So the instrument can be used with the previous settings when next turned on.

It will be understood however that test block 104 will sense the actuation of a fingerswitch on the monopolar handpiece 26, and thus the selected modulated carrier directed to the monopolar handpiece 26 will depend on which fingerswitch was depressed. While any one of the 12 modulated carriers can be hardwired or software controlled to each of the fingerswitch buttons 27 on the monopolar handpiece 26, it is also possible to build in a default mode of operation such that one of the three buttons is associated with a CUT procedure and its activation automatically selects the first or highest carrier frequency modulated with the CUT mode waveform, a second of the three buttons is associated with a CUT/COAG procedure and its activation automatically selects the first or highest carrier frequency modulated with the CUT/COAG mode waveform, and the third of the three buttons is associated with a HEMO procedure and its activation automatically selects the second or middle carrier frequency modulated with the HEMO mode waveform. Similarly, while any one of the 12 modulated carriers can be hardwired or software controlled to each of the footswitch sections 35, 36, it is preferred as a default that the left section 35 be associated with a CUT procedure and its activation automatically selects the first or highest carrier frequency modulated with the CUT mode waveform, and that the right section 36 is associated with a CUT/COAG procedure and its activation automatically selects the first or highest carrier frequency modulated with the CUT/COAG mode waveform.

These modes of operation are obtained as described in our U.S. Pat. No. 6,652,514, the contents of which are herein incorporated by reference. In that patent, resistors are incorporated into the fingerswitch handpiece with a different resistor (or absence of one) associated with each of the fingerswitch buttons. The measured resistance is communicated back to the CPU which uses the information to select a frequency and modulation mode to supply to the associated connector depending on the fingerswitch pressed. This patent also shows the use of a non-volatile memory to preserve settings and other desired information.

Normally, with the typical bipolar handpiece lacking button switches, the footswitch 34 is necessary to operate that handpiece. There also may be situations arising in which a surgeon prefers to have a bipolar handpiece with button switches. To achieve this mode of operation, it is merely necessary to enlarge the bipolar connector 23 to have four pin receptacles: two of which are used to supply the normal dual polarity bipolar electrosurgical currents, and the other two of which would be used with built in resistors as with the monopolar handpiece to communicate a particular selection to the CPU.

In operation, the ground plate 30 is always attached to the patient, and the surgeon can perform any desired monopolar or bipolar electrosurgical procedure by actuating the selection switches on the front panel.

It will be further understood that the touch panel switch user actuations can be configured to override the fingerswitch 27 or footswitch 34 selections, and thus, for example, pressing of a fingerswitch 27 will apply electrosurgical currents via the handpiece electrode to the patient's tissue as determined by the panel selections of power, carrier frequency, and electrosurgical mode. In such cases, the only functions of the fingerswitch 27 and footswitch sections 35, 36 would be to transmit to the selected active handpiece the energy supplied to the selected monopolar 22 or bipolar 23 connector.

The construction of the invention offers the advantages of ready accessibility and surprising versatility: accessibility, as the user is able to exercise either handpiece with only minor touching of the front panel, and versatility due to the achievement of any one of 12 combinations of carrier frequency and electrosurgical mode that can be made available at either handpiece, and adjustability from one electrosurgical mode to another mode is extremely simple. The actual status of the instrument can be made visible to the user by the actuation of appropriate lights or other indicators at the front panel touch switches.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical instrument for selectively providing electrosurgical currents at various carrier frequencies and in different electrosurgical modes to operate an electrosurgical handpiece, comprising:
   RF power generating circuitry configured to generate a first carrier frequency, a second carrier frequency, and a third carrier frequency, each frequency being different from any such other frequency;
   wherein the RF power generating circuitry includes a modulating circuit configured to generate at least two different modulating waveforms selected from the group of a first modulating waveform, a second modulating waveform, a third modulating waveform, and a fourth modulating waveform, each modulating waveform providing a different desired electrosurgical mode from any other such modulating wave form;
   wherein the instrument is configured to selectably output to an electrosurgical handpiece a signal representing any one or more of the two different modulating waveforms for each of at least two of the carrier frequencies, and
   wherein any combination of carrier frequency and modulated waveform is selectably outputtable to a connector for either a monopolar or bipolar electrosurgical handpiece.

2. An electrosurgical instrument according to claim 1, further comprising a footswitch connected to the instrument, said footswitch functioning to turn on and off the RF power generating circuitry.

3. An electrosurgical instrument according to claim 1, wherein the first frequency is in the range of about 3.8-4.0 MHz, the second frequency is in the range of about 1.7-2.0 MHz, and the third frequency is in the range of about 400-600 KHz.

4. An electrosurgical instrument according to claim 1, wherein the first frequency is about 4.0 MHz, the second frequency is about 1.7 MHz, and the third frequency is about 500 KHz.

5. An electrosurgical instrument according to claim 1, further comprising a monopolar or bipolar handpiece.

6. An electrosurgical instrument according to claim 1, wherein the instrument includes a first switch section controlling carrier frequency selection, a second switch section controlling mode selection, and a third switch section controlling to which handpiece selected electrosurgical signals are delivered.

7. An electrosurgical instrument according to claim 6, further comprising a monopolar handpiece connected to a first electrical connector on the instrument, a bipolar handpiece connected to a second electrical connector on the instrument.

8. The instrument of claim 1 wherein the modulating circuit is configured to generate a first modulating waveform that effects an electrosurgical mode for cutting, and the instrument is selectably configured to output the signal for the first waveform to the electrosurgical handpiece.

9. The instrument of claim 8 wherein the modulating circuit is configured to generate a second modulating waveform that effects an electrosurgical mode for coagulation, and the instrument is selectably configured to output the signal for the second waveform to the electrosurgical handpiece.

10. The instrument of claim 8 wherein the modulating circuit is configured to generate a second modulating waveform that effects an electrosurgical mode for a blend of cutting, and coagulating, and the instrument is selectably configured to output the signal for the third waveform to the electrosurgical handpiece.

11. The instrument of claim 10 wherein the instrument is configured for use with a monopolar handpiece.

12. The instrument of claim 10 wherein the first frequency is in the range of about 3.8-4.0 MHz, the second frequency is in the range of about 1.7-2.0 MHz, and the third frequency is in the range of about 400-600 KHz.

13. The instrument of claim 10 wherein the instrument is configured for use with a bipolar handpiece.

14. The instrument of claim 13 wherein the first frequency is in the range of about 3.8-4.0 MHz, the second frequency is in the range of about 1.7-2.0 MHz, and the third frequency is in the range of about 400-600 KHz.

15. The instrument of claim 8 wherein the modulating circuit is configured to generate a second modulating waveform that effects an electrosurgical mode of fulguration, and the instrument is selectably configured to output the signal for the fourth waveform to the electrosurgical handpiece.

16. The instrument of claim 15 wherein the instrument is configured for use with a monopolar handpiece.

17. The instrument of claim 15 wherein the first frequency is in the range of about 3.8-4.0 MHz, the second frequency is in the range of about 1.7-2.0 MHz, and the third frequency is in the range of about 400-600 KHz.

18. The instrument of claim 15 wherein the instrument is configured for use with a bipolar handpiece.

19. The instrument of claim 18 wherein the first frequency is in the range of about 3.8-4.0 MHz, the second frequency is in the range of about 1.7-2.0 MHz, and the third frequency is in the range of about 400-600 KHz.

20. The instrument of claim 1 wherein the modulating circuit is configured to generate a first modulating waveform that effects an electrosurgical mode for a blend of cutting and coagulating, and the instrument is selectably configured to output the signal for the third waveform to the electrosurgical handpiece.

21. The instrument of claim 20 wherein the modulating circuit is configured to generate a second modulating waveform that effects an electrosurgical mode of fulguration, and the instrument is selectably configured to output the signal for the fourth waveform to the electrosurgical handpiece.

22. An electrosurgical instrument for selectively providing electrosurgical currents at various carrier frequencies and in different electrosurgical modes to operate an electrosurgical handpiece, comprising:
RF power generating circuitry configured to generate at least one carrier frequency;
a modulating circuit configured to generate at least three different modulating waveforms on the at least one carrier frequency, each modulating waveform providing a different desired electrosurgical mode selected from the group of: (1) cutting, (2) coagulating, (3) blend of cutting and coagulating, and (4) fulguration;
wherein the instrument is configured to selectably output to an electrosurgical handpiece a signal representing any one or more of the three different modulating waveforms for the carrier frequency; and
wherein any combination of carrier frequency and modulated waveform is selectably outputtable to each of a connector for a monopolar handpiece and a connector for a bipolar electrosurgical handpiece.

23. The instrument of claim 22 wherein the instrument is configured for use with a monopolar handpiece.

24. The instrument of claim 23 wherein the RF generator is configured to generate a first frequency in the range of about (i) 3.8-4.0 MHz and (ii) a second frequency in the range of about 400-600 KHz or in the range of about 1.7-2.0 MHz.

25. The instrument of claim 22 wherein the instrument is configured for use with a bipolar handpiece.

26. The instrument of claim 25 wherein the RF generator is configured to generate a frequency in the range of about 1.7-2.0 MHz.

* * * * *